United States Patent [19]

Borch et al.

[11] Patent Number: 5,187,193

[45] Date of Patent: Feb. 16, 1993

[54] METHOD FOR STIMULATING TRANSPLANTED BONE MARROW CELLS

[75] Inventors: Richard F. Borch, Pittsford, N.Y.; Therese K. Schmalbach, Newton, Mass.

[73] Assignee: University of Rochester, Rochester, N.Y.

[21] Appl. No.: 673,089

[22] Filed: Mar. 21, 1991

Related U.S. Application Data

[63] Continuation-in-part of Ser. No. 586,304, Sep. 21, 1990, which is a continuation-in-part of Ser. No. 418,549, Oct. 10, 1990, Pat. No. 5,035,878, which is a continuation-in-part of Ser. No. 243,405, Sep. 12, 1988, Pat. No. 4,938,949.

[51] Int. Cl.$^5$ ............................................. A01N 47/10
[52] U.S. Cl. ..................................................... 514/476
[58] Field of Search .......................................... 514/476

[56] References Cited

U.S. PATENT DOCUMENTS

| | | | |
|---|---|---|---|
| 4,053,587 | 10/1977 | Davidson et al. | 424/131 |
| 4,137,248 | 1/1979 | Gale et al. | 260/429 R |
| 4,148,885 | 4/1979 | Renoux et al. | 424/162 |
| 4,426,372 | 1/1984 | Borch | 424/10 |
| 4,562,275 | 12/1985 | Speer et al. | 556/7 |
| 4,581,224 | 4/1986 | Borch | 424/10 |
| 4,594,238 | 6/1986 | Borch | 424/10 |
| 4,645,661 | 2/1987 | Schonbaum et al. | 424/10 |
| 4,680,308 | 7/1987 | Schwartz et al. | 514/492 |
| 4,721,096 | 2/1988 | Naughton et al. | 128/1 R |
| 4,938,949 | 7/1990 | Borch et al. | 424/10 |

OTHER PUBLICATIONS

Sigma Chemical Co., 1381 (1989).
K. Ikebochi et al., *PNAS USA*, 84, 9035 (1987).
B. Rosenberg, *Cancer Treatment Reports* 63: 1433-1438 (1979).
G. D. Thorn et al, *The Dithiocarbamates and Related Compounds*, (Chapter 2, pp. 7-42) Elsevier, New York (1962).
J. S. Greenberger, in *Hematopoiesis*, pp. 203-242, D. W. Golde (ed.), Churchill Livingstone, Edinburgh (1984).
T. K. Schmalbach et al., *Cancer Res.* 49: 2574-2577 (1989).
R. Qazi et al., *J. Natl. Cancer Inst.* 80: 1486-1488 (1988).
L. H. Williams et al., *Exp. Hematol.* 16: 80-87 (1988).
D. A. Juckett et al., *AACR Abstracts* 25: 322 (Abstract No. 1274) (1984).
D. L. Bodenner et al., *Cancer Res.* 46: 2751-2755 (1986).
R. G. Evans et al., *Cancer Res.* 44: 3686-3690 (1984).
J. D. Khandekar, *Res. Communications Chem. Path. and Pharmacol.* 40: 55-66 (1983).
A. Gringeri et al., *AACR Abstracts*, p. 371, Abstract No. 1471 (1984).
I. M. Pannacciulli et al., *Br. J. Cancer* 59: 371 (1989).
H. Prasad et al., *Cell and Chromosome Res.* 6: 82-84 (1983).
J. R. M. Innes et. al., *J. National Cancer Institute* 42: 1101-1114 (1969).
R. C. Gamelli et al., *Cancer Chemother. Pharmacol.* 16: 153-155 (1986).
F. W. Sunderman, Sr., *Annals Clinical Res.* 3: 182-185 (1971).
M. M. Jones et al., *Cancer Chemother. Pharmacol.* 17: 38-42 (1986).
A. Gringeri et al., *Cancer Res.*, 48, 5708 (1988).
R. I. Freshney, *Culture of Animal Cells*, Alan R. Liss, N.Y. (2d ed. 1987) at pp. 284-288.
M. Y. Gordon et al., *International J. Cell Cloning*, 1, 429 (1983).
T. Schmalbach et al., *Blood*, 76 (10 Suppl. 1) 164a (1990).

*Primary Examiner*—Douglas W. Robinson
*Assistant Examiner*—S. Saucier
*Attorney, Agent, or Firm*—Merchant, Gould, Smith, Edell, Welter & Schmidt

[57] ABSTRACT

A process is provided for obtaining one or more bone marrow cell growth factors having granulocyte/macrophage progenitor cell colony stimulating activity, said process comprising: (a) adding to the culture medium of an in vitro, established bone marrow culture a growth factor-stimulating amount of a dithiocarbamate; (b) separating the said dithiocarbamate from the in vitro treated bone marrow culture, adding fresh culture medium to said in vitro treated bone marrow culture, and permitting the concentration of said growth factor or factors to increase in said fresh culture medium; and (c) isolating said growth factor or factors from said fresh culture medium.

10 Claims, No Drawings

METHOD FOR STIMULATING TRANSPLANTED BONE MARROW CELLS

CROSS-REFERENCE TO RELATED APPLICATIONS

This application is a continuation-in-part of U.S. patent application Ser. No. 7/586,304, filed Sept. 21, 1990; which is a continuation-in-part of U.S. patent application Ser. Number 07/418,549, filed Oct. 10, 1989, which is a continuation-in-part of U.S. patent application Ser. No. 07/243,405, filed Sept. 12, 1988 (U.S. Pat. No. 4,938,949).

BACKGROUND OF THE INVENTION

At least as far back as the early 1970s, it was found that dithiocarbamates and their dimers (e.g., disulfiram) are clinically useful compounds of relatively low toxicity toward mammals. Various sulfur-containing compounds including sodium diethyldithiocarbamate (NaDDTC) have been suggested as immunostimulant medicines. See U.S. Pat. No. 4,148,885 (Renoux et al.), issued Apr. 10, 1979. Also, dithiocarbamates or their dimers have been used to inhibit the undesirable side effects of platinum compounds such as the square planer platinum (II) complexes used as antineoplastic agents. See U.S. Pat. Nos. 4,426,372 (Jan. 17, 1984), 4,594,238 (June 10, 1986), and 4,581,224 (Apr. 8, 1986), all issued to R. F. Borch. The platinum compounds useful as antineoplastic agents are not limited to platinum (II) compounds, because it has been found that platinum (IV) compounds can be administered in much the same manner as platinum (II) compounds, apparently because these six-ligand complexes break down in vivo to square planar complexes of the platinum (II) type.

The Borch method of, for example, U.S. Pat. No. 4,426,372, has been shown to be effective in clinical trials. That is, this method substantially reduces the side effects of platinum-containing drugs. These side effects include both kidney toxicity and bone marrow toxicity. For 5 mg/kg of intravenously administered platinum compound in mice, the amount of dithiocarbamic "rescue agent" is likely to be in the range of 100 mg/kg to 400 mg/kg (intravenously) and can range as high as 750 mg/kg (intraperitoneally), also in mice. A dosage of less than 50 mg/kg of body weight of dithiocarbamate is not likely to be fully effective in providing relief from or prevention of kidney damage.

Although pharmaceutically acceptable dithiocarbamic compounds such as sodium diethyldithiocarbamate (NaDDTC) and disulfiram have relatively high $LD_{50}$ values and are not considered highly toxic to mammals, there are scattered reports in the literature regarding strange behavior exhibited by rats or mice injected with NaDDTC. The true import of this literature became fully apparent during clinical trials of NaDDTC as a "rescue agent", i.e., as an agent for the reduction of side effects from the administration of platinum compounds. These clinical trials demonstrated that human patients given dosages of NaDDTC effective for "rescue" purposes (e.g., dosages on the order of 50–150 mg/kg of body weight) experienced extremely unpleasant effects which caused them to feel panic and discomfort. It was necessary to develop a technique of administration of the NaDDTC whereby the patient is sedated prior to receiving the dithiocarbamate.

All available evidence indicates that the panic reaction to dithiocarbamates resulting from dosages of, for example, 50–150 mg/kg is not the result of any life-threatening process occurring in the body of the patient, nor is there any evidence of permanent or chronic effects or damage resulting from NaDDTC administration. After the course of dithiocarbamate administration has been completed, patients returned to normal and no sequelae of the panic reaction are observed. Moreover, it presently appears that some hydroxy-substituted analogs of NaDDTC may be even less toxic than NaDDTC itself. Nevertheless, further improvement in the treatment of toxic side effects of useful cytotoxic compounds is desirable.

As noted previously, much less is known about treatments for bone marrow toxicity. Some anti-cancer drugs, both platinum-containing and platinum-free, can seriously damage the blood-forming function of the bone marrow—an effect sometimes referred to as myelosuppression. Among the drugs causing significant myelosuppression effects are cytotoxic antibiotics and antibiotic derivatives, other cytotoxic drugs, antimetabolites (which inhibit processes involved in DNA formation), alkaloid-type anti-tumor agents, alkylating agents, and heavy metal complexes (particularly Pt complexes such as "Carboplatin"). A method to produce protective factors to counteract or to protect against the side effects of these drugs would be a highly welcome addition to the field of cancer treatment.

SUMMARY OF THE INVENTION

The present invention provides a process for obtaining one or more bone marrow cell growth factors, e.g., those having granulocyte/macrophage progenitor cell colony stimulating activity, (GM-CSA) said process comprising:

(a) adding to the culture medium in an in vitro, established bone marrow culture a growth factor-stimulating amount of a dithiocarbamate compound of the formula (I):

wherein $R^1$ and $R^2$ are the same or different lower aliphatic or cycloaliphatic or heterocycloaliphatic groups, unsubstituted or substituted by hydroxyl, or one of $R^1$ and $R^2$, but not both, can be H, or $R^1$ and $R^2$, taken together with the N atom, can be a 5- or 6-member N-heterocyclic ring which is aliphatic or aliphatic interrupted by a ring oxygen or second ring nitrogen, and M is H or one equivalent of a pharmaceutically acceptable cation, in which case the rest of the molecule is negatively charged, or M is

wherein $R^3$ and $R^4$ are defined in the same manner as $R^1$ and $R^3$ thereby obtaining an in vitro treated bone marrow culture;

(b) separating the said compound from the in vitro treated bone marrow culture, adding fresh culture medium to said in vitro treated bone marrow culture, and permitting the concentration of said growth factor or factors to build up in said fresh culture medium;

(c) after an effective period of time, e.g., after about 8 but less than about 96 hours, separating the said fresh culture medium from the in vitro treated bone marrow culture, thereby isolating said growth factor or factors from the in vitro treated bone marrow culture.

Preferably, about 0.03-1.0 mmoles/l of medium of the dithiocarbamate will be employed to stimulate the production of growth factor(s), most preferably about 0.03-0.2 mmole/l of culture medium.

For example, treatment of human long term bone marrow cell cultures (HLTBMC) in accord with the invention with 30 µM sodium diethyldithiocarbamate (DDTC) for one hour enhanced the production of a number of hematopoietic cytokines, as shown on Table 1, below.

TABLE 1

ENHANCED HLTBMC PRODUCTION OF HEMATOPOIETIC CYTOKINES FOLLOWING TREATMENT WITH DDTC

| Cytokine | Enhancement | Time of Peak |
|---|---|---|
| TNF-α | 5-fold | 6 hr |
| IL-6 | 3-fold | 12 hr |
| IL-1β | >100-fold | 24 hr |
| G-CSF | 50-fold | 24 hr |
| GM-CSF | 12-fold | 24 hr |

Furthermore, the formation of GM-CFC (Granulocyte/Macrophage colonies) was enhanced about 18-fold by treatment of fresh human bone marrow cells with DDTC-treated HLTBMC supernatants collected at 12, 24, and 48 hr after DDTC exposure (30 µM, 1 hr).

The present invention also encompasses bone marrow cell growth factors produced by the present process, as well as pharmaceutical dosage forms of said factors in a pharmaceutically acceptable medium. The present invention further comprises a method for the in vivo stimulation of one or more bone marrow cell growth factors, e.g., to treat damage to, or to stimulate, the blood-forming function of the bone marrow of a living mammal by administering an effective amount of one or more of said pharmaceutical dosage forms, or by administering an effective amount of a dithiocarbamate of formula I.

Dithiocarbamic compounds of the formula I are surprisingly effective for the stimulation of, or for the treatment of damage to, the blood-forming function of the bone marrow of a living mammal when administered in doses which preferably do not cause the panic response described previously. This discovery is disclosed and claimed, for example, in parent application Ser. No. 07/418,549 and in Borch et al. (U.S. Pat. No. 4,938,949), the disclosures of which are incorporated by reference herein. Amounts of dithiocarbamic compounds in excess of 30 mg/kg of body weight of small mammals (e.g., mice) are not needed in this invention, and would be very excessive for large mammals such as humans particularly in the case of damage caused by anticancer drugs, e.g., platinum-containing drugs. At least some beneficial response to the dithiocarbamic compound is observable even in small mammals at dosage levels in the microgram/kg range. Thus, a suitable dosage unit according to this invention can be in the range of about 0.001 to 30 mg per kilogram of body weight of the mammal, more preferably above about 0.003 and up to about 10 mg/kg of body weight.

The therapeutic effect of the dithiocarbamic compounds described above is not limited to treating damage caused by platinum-containing drugs. Mammals given platinum-free myelosuppressive antineoplastic drugs, subjected to irradiation, or that suffer from blood disorders such as aplastic anemia, can also be successfully treated with an effective amount of one of these dithiocarbamate salts or dimers (or, less preferably, acids, i.e. where M=H). The preferred dosage units for treating the side effects of these platinum-free drugs, and for stimulating the growth of bone marrow cells which have been damaged or compromised by other treatments or pathologies, are the same as for the platinum-containing drugs, but dosages up to 300 mg/kg in mice (up to 75 mg/kg in humans) appear to be tolerated when adequate precautions are utilized, e.g., sedation.

As will be explained subsequently, guidelines for converting these dosage units into mg/m$^2$ have been discovered, both for large mammals, such as humans, and small mammals, such as mice. In principle, mg/m$^2$ dosing is equivalent in all species, including both large and small mammals. It has also been found that the gap between a suitable mg/kg dosage unit for a small mammal and a suitable mg/kg dosage unit for a human is somewhat less than might have been predicted by a skilled pharmacologist.

These very low dosages are believed to be well below stoichiometric levels and bear more resemblance to amounts at which catalysts are employed. Surprisingly, improvement in the blood-forming function of normal bone marrow is rather minimal when the dithiocarbamic compounds of this invention are administered to a healthy mammal. However, very significant improvements in bone marrow function are observed when the bone marrow of the mammal has been damaged, e.g., by administration of anti-neoplastic, e.g., cytotoxic drugs, by irradiation or by certain diseases. Accordingly, the therapeutic method of this invention applies primarily to mammals who have already suffered some myelosuppression effects. However, because there may be some time delay involved in observing the beneficial effects of this invention, it is possible to administer the dithiocarbamic compound more or less simultaneously with the myelosuppression-causing agent (i.e., the drug or radiation or the like). Typically, the dithiocarbamic compound will be administered prior to, and continued after the myelosuppression-causing agent has been given to the patient.

The preferred dithiocarbamic compounds used in this invention are those of the aforementioned formula (I), $R_1R_2NCSSM$, wherein M is a pharmaceutically acceptable cation, and $R_1$ and $R_2$ are lower aliphatic or hydroxy-substituted lower aliphatic groups (e.g., a polyhydroxy-substituted lower $C_3$–$C_6$-alkyl group or a ($C_2$–$C_6$)-alkyl). The preferred route of administration of these compounds (particularly when M is a metallic cation) is parenteral, e.g., intravenously, and a suitable unit dosage can be dissolved, suspended, or otherwise combined with a pharmaceutically acceptable carrier such as an aqueous medium. In the case of the dimers (e.g., disulfiram), which are far less water soluble, the preferred route of administration is oral.

DETAILED DESCRIPTION

Most of the discussion which follows is related to the use of dithiocarbamates to produce bone marrow cell growth factors or to protect against the bone marrow toxicity of anti-cancer drugs or radiation. However, it will be understood that the method and compounds of this invention can find application whenever the blood-forming function of the bone marrow of a living mammal has been damaged or inhibited. For example, the present treatment method can be used to stimulate the production of blood-forming bone marrow cells in the case of a bone-marrow transplant recipient, most of, or all of whose autologous bone marrow cells have been destroyed prior to marrow transplantation. Stimulation of the blood-forming bone marrow cells is also desirable in the treatment of diseases such as hypoplastic anemia. As noted previously, clinical use of the method and dosage units of this invention can be carried out in combination with known antitumor agents and can be more or less simultaneous with (or even previous to) the administration of the antitumor agent, although typically the antitumor agent will be administered first. It is generally desirable that, when the antitumor agent is administered first, the dithiocarbamate is given to the treated mammal within three hours.

Myelosuppression (toxicity to the blood-forming cells of the bone marrow) is a serious and frequently doselimiting side effect of most cancer drugs used in the cancer clinic today. Because these are rapidly dividing cells, they are particularly susceptible to the toxic effects of the drug used to control diseases of cell proliferation. The stem cell is the most primitive of the bone marrow cells; it represents less than 0.1% of the cells of the marrow, yet it is capable of differentiating to produce progenitor cells for all of the blood cell lines (red cells, lymphocytes, granulocytes, and platelet precursors). The stem cell is also a self-replenishing cell in that it can undergo division to generate additional stem cells. Although stem cells have been only recently specifically isolated and characterized, and then only in mice, an estimate of their numbers can be obtained using the spleen colony assay (CFU-S). Maintenance of an appropriate population of stem cells is obviously critical to survival of mammals and perhaps other organisms.

The granulocyte precursor is one of the most important and frequently damaged progenitor cell in the bone marrow. Its clinical importance lies in the role that the granulocyte plays in fighting infections. Patients with markedly reduced granulocyte counts resulting from cancer chemotherapy are highly susceptible to infection from a variety of organisms and, if bone marrow function does not recover quickly enough, they can succumb to infection rather than the primary malignancy for which they have been receiving treatment. The granulocyte precursor derives from differentiation of a stem cell; this precursor can undergo subsequent amplification and differentiation to produce a mature granulocyte. The granulocyte precursor is more abundant in the marrow than the stem cell, and its numbers can be estimated using the granulocyte/macrophage progenitor cell (GM-CFC) assay.

Mechanistic studies done in connection with this invention reveal that anticancer drugs which inhibit tumor growth through interference with DNA synthesis (and which have the unfortunate effect of interfering with DNA synthesis in bone marrow also) are significantly modulated in their effect upon DNA synthesis in bone marrow when the dithiocarbamate is administered after the anti-cancer drug, e.g., three hours afterward. The mechanism of bone marrow protection provided by the dithiocarbamates is different from that involved in the reversal of other toxicities (e.g., kidney toxicity) and is not dependent upon stoichiometric displacement of platinum from biochemical structures. For example, the basis for the present process claims is our discovery that dithiocarbamates selectively stimulate proliferation of bone marrow cells in vitro. However, dithiocarbamates such as sodium diethyldithiocarbamate (DDTC) do not alter the number of bone marrow cells proliferating in vivo in the absence of myelotoxic insult.

TREATABLE BONE MARROW DAMAGE

As noted previously, antineoplastic agents and treatment techniques are a particularly important cause of myelosuppression. These antineoplastic treatments fall into two broad categories: radiation therapy and drugs. The drugs which have adverse effects upon blood formation (e.g., bone marrow toxicity) fall into several categories including cytotoxic antibiotics isolated from cultures of various species of Streptomyces and derivatives of such antibiotics (bleomycin, daunorubicin, dactinomycin, doxorubicin hydrochloride (adriamycin)), other cytotoxic agents which are not necessarily antibiotic derivatives, antimetabolites such as 5-fluorouracil, cytarabine, methotrexate, and thioguanine; alkaloid-type compounds including alkaloids extracted from natural sources such as the periwinkle plant and similar herbs (vincristine sulfate, vinblastine sulfate), DNA synthesis inhibitors and DNA crosslinkers which can be, for example, alkylating agents such as thiotepa or busulfan, or heavy metal complexes (such as the platinum complexes discussed previously), and compounds containing the 2-chloroethyl group (typically, a 2-chloroethyl group attached to a nitrogen atom). There are compounds presently in clinical use which fall into none, or into more than one of these categories. For example, etoposide acts on one enzyme, topoisomerase, which is involved in controlling DNA configuration. Also, an antibiotic derivative of a 2-chloroethyl-containing compound or a cytotoxic agent can be a DNA synthesis inhibitor and/or an alkylating agent. In some cases, the mode of action of an antineoplastic drug is unknown, e.g., in the case of dacarbazine.

There is a considerable variety of antineoplastic agents which have the 2-chloroethyl (i.e., the beta-chloroethyl) group, typically attached to a nitrogen atom. Among these are lomustine. Some of these compounds are derivatives of L-amino acids, some are derivatives of steroids, some are monocyclic compounds, some are aliphatic amine derivatives, and still others are urea derivatives (including nitrosourea derivatives). Compounds of the nitrosourea type typically have the following formula:

Cl—CH$_2$CH$_2$—N(NO)—CO—NH—R* wherein R* is an organic group such as an aliphatic or cycloaliphatic radical or a second 2-chloroethyl group. One widely used compound of this type is 1-3-bis(2-chloroethyl)-1-nitrosourea, also known as BCNU or BiCNU or carmustine.

In antineoplastic drugs containing the 2-chloroethyl group, the bis-(2-chloroethyl)-amino functional group is particularly common, e.g., as in chlorambucil or cyclophosphamide. This bis-substituted group has the formula (ClCH$_2$CH$_2$)$_2$N- and can be substituted directly on an aliphatic chain or an aromatic or cycloaliphatic or heterocycloaliphatic ring (or indirectly, whereby N is part of a carbamate linkage or the like). The so-called "nitrogen mustard" derivatives typically contain the bis-(2-chloroethyl)-amino group and can be highly toxic if not carefully administered.

Of the agents which inhibit DNA synthesis or cross-link DNA molecules, the platinum (II) and (IV) compounds are among the most promising for clinical use. For a discussion of the types of platinum-containing drugs contemplated by Borch for use in combination with dithiocarbamic compounds, see (in addition to the three Borch patents) U.S. Pat. No. 4,053,587 (Davidson et al.), issued Oct. 11, 1977; U.S. Pat. No. 4,137,248 (Gale et al.), issued Jan. 30, 1979; U.S. Pat. No. 4,562,275 (Speer et al.), issued Dec. 31, 1985; U.S. Pat. No. 4,680,308 (Schwartz et al.), issued July 14, 1987, and similar references appearing in both the patent and scientific literature, e.g., the series of papers regarding platinum treatment of tumors and resulting side effects in *Cancer Treatment Reports*, 63, 1433 (1979). The compound "cisplatin" (cis-dichlorodiammine platinum [II]) is very effective against testicular and ovarian tumors but has been found to have myelosuppressive effects in 25-30% of patients treated with this drug. More recent developments in platinum (II) and platinum (IV) anticancer drugs have produced compounds which are not only very effective against tumors but are also substantially free of side effects other than myelosuppression. Cisplatin, on the other hand, has significant kidney toxicity effects as well as bone marrow toxicity.

Of the nitrogen-containing platinum monodentates and bidentates myelosuppression can occur when the ligands include ammonia, diaminocyclohexane and its derivatives, alkylene and diamines (e.g., ethylenediamine), alkyl-substituted amines, $C_3$- and $C_5$-cycloalkyl amines, and the like. Suitably selected tetravalent Pt complexes can behave like Pt(II) complexes after administration to a living organism. Removal of axial ligands in vivo accounts for the Pt(II)-like activity, at least to some extent. A particular preferred species of Pt(IV) complex is chlorohydroxy-isopropylamine-platinum ("CHIP"). "CHIP", like other "second-generation" platinum-containing therapeutic agents is low in kidney toxicity compared to the "first generation" agents but, unfortunately, is high in bone marrow toxicity.

Various Pt(II) compounds of demonstrated antitumor utility, e.g., "TNO-6" and "CBDCA" (see U.S. Pat. No. 4,137,248) also showed increased bone marrow toxicity. These otherwise desirable Pt(II) compounds can be characterized by the formula:

$$(R'NH_2)(R''NH_2)Pt(X^1)(X^2)$$

where $X^1$ and $X^2$ are the same or different and are halogen, OH, water, carboxyl, sulfato, or sulfate, or, taken together, the residue of a polycarboxylic acid; $X^1$ and $X^2$ preferably are $SO_3H$ or $—CO_2—$, particularly as the residue of a polycarboxylic acid such as 1,1-cyclobutane-dicarboxylic acid, trimellitic acid, etc; R' and R" are the same or different and are halogen or an aliphatic group, or taken together, the aliphatic residue of a heterocyclic moiety which includes both N-atoms.

DITHIOCARBAMIC COMPOUNDS

The term "dithiocarbamic compounds" or dithiocarbamates as used in this application is intended to refer to compounds containing the functional group $R_1R_2N—CS—S—$, wherein $R_1$ and $R_2$ are the same or different and represent different aliphatic or cycloaliphatic or heterocycloaliphatic groups, e.g., $(C_1-C_6)$alkyl, $(C_5-C_{10})$ cycloalkyl or five- to ten-membered heterocyclic groups, unsubstituted or substituted by hydroxyl. One of the two groups, $R_1$ and $R_2$, but not both, can be hydrogen. Alternatively, $R_1$ and $R_2$, taken together with the N-atom, can be a 5- or 6-member N-heterocyclic ring which is aliphatic or aliphatic interrupted by a ring oxygen or a second ring nitrogen.

When the group $R_1R_2N—CS—S—$ is part of a dimer such as disulfiram, the dangling valence bond is linked to a group of the formula $—S—CS—NR_3R_4$, wherein $R_3$ and $R_4$ are defined in the same manner as $R_1$ and $R_2$. When the group $R_1R_2N—CS—S—$ is an anion, the cation can be of the ammonium-type or can be derived form a monovalent or divalent metal such as an alkali or alkaline earth metal, cations which provide good water solubility and low toxicity being preferred, e.g., $Na^+$, $K^+$, $Zn^{++}$ and the like. In the case of the dithiocarbamic acids, the group $R_1R_2N—CS—S—$ is linked to a hydrogen atom which is ionizable, particularly at a pH above about 5. Since the dithiocarbamic acids are not very stable in vitro, it would appear to be only marginally operative, and not advantageous, to use the dithiocarbamic acid form of the myelosuppression treatment agents of this invention. However, these acids are generally soluble in polar organic solvents such as alcohol, and they would have some tendency to form stable alkali metal salts in body fluids.

Dithiocarbamates and related compounds have been reviewed extensively in a work by G. D. Thorn et al. entitled "The Dithiocarbamates and Related Compounds," Elsevier, New York, 1962. As explained in Chapter 2 of Thorn et al., the preparation of dithiocarbamates is very simple The compounds of the formula $R_1R_2NCSSH$ or $R_1R_2NCSSNa$ can be formed by reaction of carbon disulfide with a secondary amine, typically in alcoholic or aqueous solution. The usual practice is to carry out this reaction in the presence of NaOH, so that the sodium dithiocarbamate salt is formed. Thus, for example, sodium dimethyl dithiocarbamate is formed from $CS_2$, NaOH and dimethylamine. See Thorn et al., page 14, and the references cited therein. Other typical dithiocarbamic compounds disclosed and characterized in Thorn et al. include:

N-methyl,N-ethyldithiocarbamates, hexamethylenedithiocarbamic acid, sodium di(beta-hydroxyethyl) dithiocarbamate, various dipropyl, dibutyl and diamyl dithicarbamates, sodium N-methyl,N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, alpha-furfuryl dithiocarbamates and imidazoline dithiocarbamates.

Another interesting type of dithiocarbamate which appears to have significant biovailability and biocompatibility includes compounds wherein R of the structure $R_1R_2N—CS—S—$ is a hydroxy-substituted or, preferably, a polyhydroxy-substituted lower alkyl group having up to 6 carbon atoms. For example, $R_1$ can be $HO—CH_2—CHOH—CHOH-CHOH—CHOH—CH_2—$. In such compounds, $R_2$ can be H or lower alkyl (unsubstituted or substituted with one or more hydroxyl groups). Steric problems can, of course, be minimized when $R^2$ is H, methyl, or ethyl. Accordingly, a particularly preferred compound of this type is an N-methyl-glucamine dithiocarbamate salt, the most preferred cations of these salts being sodium or potassium.

The term "lower" (as in "lower alkyl" or "lower aliphatic"), as used in this discussion, refers to radicals having one to six carbon atoms. Water solubility and/or biocompatibility problems can be greatly increased when the number of carbon atoms exceeds six. Of the unsubstituted alkyl groups, the ethyl radical appears to provide a high level of water solubility coupled with relatively low toxicity. Nevertheless, compounds such as sodium diethyldithiocarbamate (NaDDTC) are not necessarily well tolerated by humans and other mammals (even smaller mammals) when administered at levels above 50 mg/kg of body weight. Patients complain of flushing and tightness in the chest during infusion of NaDDTC, and they develop symptoms of acute anxiety. These symptoms subside rapidly and without sequelae after the infusion is stopped, and the symptoms can be alleviated somewhat (but not abolished) by pretreatment sedatives. In the scientific literature, there are occasional references to analogous effects in rats, and these effects are sometimes referred to as the "rat rage" syndrome. A major advantage of this invention is that the "rat rage" syndrome can be avoided entirely due to the surprising efficacy of dosage units of this invention.

The dithiocarbamate derivative of N-methyl glucamine (e.g., sodium N-methylglucamine dithiocarbamate) was synthesized in 1984 and has been shown to inhibit the nephrotoxicity of the compound "cisplatin" (cis-dichlorodiammine platinum [II]). Moreover, the polyhydroxylated side chain appears to reduce somewhat the dithiocarbamate side effects described above.

Other preferred dithiocarbamates include the alkali or alkaline earth metal salts wherein the anion is di-n-butyldithiocarbamate, di-n-propyldithiocarbamate, pentamethylenedithiocarbamate, and tetramethylene dithiocarbamate and those compounds wherein $R_1$ and/or $R_2$ of the formula $R_1R_2N—CS—S—$ is a beta-hydroxyethyl. Generally speaking, the greater the solubility in polar solvents (particularly in aqueous media), the more convenient the administration of the dithiocarbamic myelosuppression treatment agent can be, because parenteral administration is particularly preferred in the method of this invention, and solutions (particularly aqueous solutions) are more convenient to administer than suspensions.

For this reason, the monomeric dithiocarbamic compounds are preferred over the dimeric analogs. Disulfiram is commercially available and has been used in the treatment of alcoholism to help the patient remain in a state of self-imposed sobriety. This treatment is carried out by oral administration of disulfiram in tablet form. Disulfiram has relatively low solubility in polar solvents, whereas diethyldithiocarbamate monomeric salts and hydroxysubstituted alkyl dithiocarbamate monomeric salts are highly soluble in water, e.g., in molar quantities, and are also soluble in alcohol.

Other parenteral modes of administration can be used, e.g., intramuscular injection or introduction through the intraperitoneal route. Oral administration can also be employed to administer dithiocarbamates in accord with the present method. However, the dosage units of this invention are most effective by the intravenous route.

DOSAGE UNITS AND FORMS

It is very common in pharmacology to express dosage units in mg/kg (i.e., mg/kg of body weight) or, if a continuing series of doses over many days is contemplated, mg/kg per day. A mg/kg dosage unit is reasonably constant for any given species of mammal. However, an average effective dose can vary from species to species, due to differences in metabolic rates. Smaller mammals such as rats and mice metabolize drugs (convert the drugs to other compounds in vivo) more effectively than larger mammals such as dogs and humans. Theoretical studies of drug metabolic rates in general tend to confirm that there is a rough inverse correlation between drug metabolic rate and the surface area of the body of the mammal. In principle, then, a dosage expressed in mg/m$^2$ would be roughly equivalent in all species, regardless of body area, i.e., an $ED_{50}$ of 100 mg/m$^2$ in a human would also be 100 mg/m$^2$ in a mouse. To convert mg/kg to mg/m$^2$, one multiplies by a constant for the desired species which is a function of the surface area of a member of that species, thus:

Dose in mg/m$^2$ = Constant × dose in mg/kg.

The constant for human, dog, rat and mouse species are, respectively; 37, 20, 5.2, and 3.0. Expressed in relative terms, the human constant is almost twice the dog constant (1.9), the human constant is over 7 times the rat constant, and the human constant is 12.3 times the mouse constant. The dosage unit for NaDDTC administered to mice to ameliorate the kidney toxicity of Cisplatin (750 mg/kg, preferably >200 mg/kg) works out to be, for example, 3.0×200 mg/kg=600 mg/m$^2$, more typically 3.0×300 mg/kg=900 mg/m$^2$. Theoretically, then, the typical human dosage unit would be 900 mg/m$^2$ divided by 37=about 25 mg/kg. In other words, theory would predict that the human dose in mg/kg would be about one-twelfth of the dose for mice. In actual practice, however, it has been found that the human dose of NaDDTC can be as much as a sixth to a third, e.g., one-fourth of the dose for mice; hence, a dose in mice of, for example, 30 mg/kg works out in practice to be 5 to 10 mg/kg, most typically 7.5 mg/kg for humans. In the present invention, a dosage of 0.3 mg/kg (1 mg/m$^2$) can provide some useful effect in humans and has even been observed to show some bone marrow-restoring effect in mice. A reliable effective dose range is, for example, about 1.0 to about 145 mg/m$^2$, more preferably 130 mg/m$^2$, regardless of species. For all species, the dosage of 130 mg/m$^2$ is ample and may be unnecessarily large. Suitable dosage units can be less than 90 mg/m$^2$ or, if desired, less than 75 mg/m$^2$. For humans, dosage units in mg/kg are best calculated by dividing the mg/kg dose for mice by about 4 (instead of by 12.3). Accordingly, a dose for mice of, say, 30 mg/kg would work out to about 7.5 mg/kg in a human, and a dose for mice of 10 mg/kg would work out to about 2.5 mg/kg in a human.

In the treatment of myelosuppression, dithiocarbamic treatment agents of this invention exhibit a rather typical sigmoidal logarithmic dose-response curve, but the placement of this curve with respect to the dose and response axes is surprising. To obtain a typical logarithmic dose-response curve, the percent of surviving stem cells in the test animals is indicated by the ordinate, and the dosage is indicated in 10-fold intervals ($\log_{10}$ dose units) with respect to the abscissa. The resulting plot shows that optimal bone marrow protection can be obtained at dosages well below 50 mg/kg of body weight, and even at well below 30 mg/kg. A response can be observed at extremely low dosages (above submicrogram/kg levels but still below 3 µg/kg, e.g., about 1 µg/kg), and significant protection appears to be obtained, even in mice, at dosages as low as 3 µg/kg, i.e., 0.003 mg/kg. Dosages approaching 30 mg/kg (even in mice) appear to be unnecessarily high in the context of the method of this invention, hence a preferred range for a dosage unit of this invention is about 0.3 to 10 mg/kg of body weight of the mammal. The "flat" portion of the sigmoidal curve appears to be reached at dosages as low as 0.3 mg/kg, but it can be desirable to exceed this dosage level in order to provide assurance that efficacy will be high. A particularly preferred upper limit for the human dose appears to be about 10 mg/kg, more preferably 3.0 or even 2.5 mg/kg. When the dosage units are in mg/m$^2$, a useful range is, for example, 1-200 mg/m$^2$, more preferably about 1-75 mg/m$^2$, as explained previously.

A particularly preferred form of a dosage unit of this invention is obtained by dissolving a dithiocarbamate salt in an aqueous medium (e.g., normal saline), measuring out a dosage unit in the range of 0.001 to 30 mg per kilogram of body weight of the mammal to be treated, and sealing the resulting dosage unit in a vial (e.g., a glass or plastic vial) adapted for use in a conventional intravenous administration technique. Alternatively, the dosage unit can be dissolved in a conventional plastic intravenous drip bag, in which case the dosage unit can be diluted with an aqueous solution of a typical intravenous administration fluid. (The potential chelating or complexing effects of the dithiocarbamic compound should be taken into account, with respect to such fluids.)

Alternatively, a dosage unit of the dithiocarbamic compound can be extended with a standard solid pharmaceutically acceptable extender (e.g., mannitol) and packaged in dosage unit form for solution later on in a fluid suitable for intravenous administration. Adjuvants, excipients, and the like can be included.

A particularly preferred unit dosage of this invention comprises about 0.01 to about 10 mg/kg of the dithiocarbamic myelosuppression treatment agent, the treatment agent being dissolved in a liquid pharmaceutically acceptable carrier comprising an aqueous medium. Other suitable pharmaceutically acceptable carriers are available to those skilled in the art.

The principle and practice of this invention is illustrated in the following non-limiting Examples.

EXAMPLE I

BDF$_1$ mice were used and the drugs were administered by intravenous (iv) injection in the tail vein. Sodium diethyldithiocarbamate (DDTC) was administered at various dosages 3 hours after administration of an anticancer drug. Bone marrow cells were harvested 24 hours after anticancer drug treatment (21 hours after NaDDTC). Toxicity to stem cells was evaluated using the spleen colony (CFU-S) assay; toxicity to granulocyte progenitors was evaluated using an in vitro clonogenic (CFU-GM) assay. To provide controlled studies, mice were randomly divided into four groups of four animals each; one group served as a no-treatment control, one group received DDTC alone (the "DDTC group"), one group received anticancer drug alone (the "drug-only group"), and one group received anticancer drug followed by DDTC 3 hours later (the "drug and DDTC group"). Twenty-four hours after drug treatment, the mice were killed by cervical dislocation, the femurs were removed, and the marrow cells were flushed out of the bone and counted.

For the CFU-S assay, 5-15×10$^4$ cells were injected via the tail vein into recipient mice that had just received a bone marrow lethal dose of radiation. Twelve days after injection of donor marrow cells, the mice were killed by cervical dislocation, the spleens were removed, and the colonies of cells growing on the surface of the spleen were counted. The data are normalized to represent the number of colonies formed/10$^5$ cells injected and are reported as the percent of colonies formed compared to the control group.

For the CFU-GM assay, 2-4×10$^4$ bone marrow cells from the treated groups were plated on soft agar. After incubating for 7 days, the colonies containing at least 50 cells were counted; in representative experiments, the colonies were removed and the cell type determined. The data are reported as the percent of colonies formed compared to the control group.

The data obtained from the DDTC group and the no-treatment group tends to confirm that DDTC has little or no stimulant effect upon healthy bone marrow in vivo. That is, DDTC has negligible effects on the stem cell and granulocyte precursor populations in normal mouse bone marrow. The colony counts for the DDTC group were within 10% of no-treatment group values for both CFU-S and CFU-GM in all cases. In the drug-only group, dose-dependent toxicity toward both CFU-S and CFU-GM was observed for carmustine (BCNU) and adriamycin. In the drug and DDTC group, DDTC provided significant protection against BCNU toxicity t both stem cells and granulocyte progenitors at all doses of BCNU tested. In the case of adriamycin, reduction of toxicity was observed at all doses but was less impressive at the highest adriamycin dose tested.

The situation in the case of mitomycin (an anti-cancer drug of the antibiotic type) is more complicated because it is particularly difficult to prevent or reverse the myelosuppressive effects of this drug.

Very good results were obtained when the drug+DDTC group was given carboplatin (a platinum-containing anticancer drug) followed by various doses of DDTC. Carboplatin given to the drug-only group resulted in mice having CFU-S values which were only 10% of the control group level. When the CFU-S assay shows 30% or more of the value of the control (no treatment) group, this is considered indicative of very good activity against myelosuppression. The 30% level in the drug+DDTC group was achieved with an iv dose of 30 mg/kg of NaDDTC, but 40% of the control CFU-S level was also achieved with an iv dose of only 0.3 mg/kg of NaDDTC.

In the experiments summarized in Table 2 (which were conducted according to the procedure described above), the dose of NaDDTC was 300 mg/kg of body weight, which appears to be excessive, but which illustrates the efficacy of dithiocarbamate, vis-a-vis damage from platinum-free drugs. Both in Part A (drug=BCNU) and in Part B (drug=adriamycin), data are given for the "DDTC group", the "drug-only group", and the "drug and DDTC group". These data are set forth in Table 2, below.

TABLE 2
EFFECT OF NaDDTC ON DRUG-INDUCED MYELOSUPPRESSION

|  | Drug Dose (mg/kg) | Mouse Group | CFU-S(%) | CFU-GM(%) |
|---|---|---|---|---|
| Part A | — | DDTC | 102 ± 2 | 102 ± 1 |
| Drug: | 20 | Drug-only | 47 ± 6 | 83 ± 2 |
| BCNU | 20 | Drug and DDTC | 57 ± 12 | 99 ± 2 |
|  | — | DDTC | 101 | 103 ± 2 |
|  | 40 | Drug-only | 30 ± 1 | 43 ± 2 |
|  | 40 | Drug and | 50 ± 1 | 83 ± 2 |

TABLE 2-continued
EFFECT OF NaDDTC ON DRUG-INDUCED MYELOSUPPRESSION

| | Drug Dose (mg/kg) | Mouse Group | CFU-S(%) | CFU-GM(%) |
|---|---|---|---|---|
| | | DDTC | | |
| | — | DDTC | 114 | 102 ± 2 |
| | 65 | Drug-only | 19 ± 2 | 25 ± 1 |
| | 65 | Drug and DDTC | 49 ± 11 | 64 ± 1 |
| Part B | — | DDTC | 106 | 102 |
| Drug: | 18 | Drug-only | (21) | 37 ± 6 |
| Adriamycin | 18 | Drug and DDTC | (42) | 45 ± 2 |
| | — | DDTC | — | 102 ± 1 |
| | 24 | Drug-only | 40 | 32 ± 1 |
| | 24 | Drug and DDTC | 52 | 42 ± 2 |
| | — | DDTC | — | 102 |
| | 32 | Drug-only | 29 ± 8 | 20 ± 5 |
| | 32 | Drug and DDTC | 57 ± 7 | 28 ± 2 |

The following experiments were conducted to demonstrate the production of bone marrow cell growth factor(s) with DDTC, wherein Cis-diammine(cyclobutanedicarboxylato)-platinum (II), or "CBDCA" was obtained from Johnson-Matthey, Inc. (Malvern, Pa). Sodium diethyldithiocarbamate (DDTC) and bovine serum albumin (BSA) were obtained from Sigma Chemical Company (St. Louis, Mo.). Fischer's medium, McCoy's 5A medium with L-glutamine, IMDM, minimum essential medium alpha modification ($\alpha$-MEM) L-glutamine (100X), pokeweed mitogen, sodium bicarbonate (7.5% solution), sodium pyruvate (100X), vitamin solution (100X), essential amino acid solution (50X), non-essential amino acid solution (100X), gentamicin, penicillin/streptomycin solution, and antibiotic-/antimycotic solution were purchased from GIBCO (Grand Island, N.Y.). Horse serum and fetal bovine serum were purchased from Hyclone Laboratories (Logan, Utah). Salmonella typhosa lipopolysaccharide B (LPS) was purchased from Difco Laboratories (Detroit, Mich.). Methylcellulose (4A premium grade) was provided by Dow Chemical Company (Midland, Mich.). Falcon Petri plates and microscope slides were obtained from Fisher Scientific Company (Springfield, N.J.). All other plastic culture supplies and test tubes were obtained from VWR (Rochester, N.Y.). Ficoll-Paque was purchased from Pharmacia, Piscataway, N.J., GM-CSF and IL-6 ELISA kits were purchased from Genzyme Inc., Boston, Mass.; granulacyte colony stimulating factor (G-CS) ELISA kits were obtained from Amgen, Inc., Thousand Oaks, Calif. IL$\beta$ and TNF-$\alpha$ ELISA kits were purchased from Cistron Biotechnology, Pine Brook, N.J.

EXAMPLE II

Enhancement of GM-CSA in Murine Long Term Bone Marrow Cell Cultures

A. Experimental Animals Male 6- to 8-week-old C57BL/6J x DBA/2J mice were obtained from The Jackson Laboratories (Bar Harbor, Me.). Mice were housed 10/cage in plastic cages and allowed food and water ad libitum. All mice were acclimated for at least 7 days; the animals were then killed by cervical dislocation and both femurs and tibias were harvested for these experiments.

B. Establishment of Murine Long Term Bone Marro Cultures (LTBMC). Long-term bone marrow cultures were established according to J. S. Greenberger, in Hematopoiesis, D. W. Golde, ed., Churchill Livingstone, Edinburgh (1984) at pages 203-242. One ml of growth medium [Fisher's medium (pH 7.0) supplemented with 25% horse serum, 100 U/ml penicillin G, and 100 $\mu$g/ml streptomycin] was used to aseptically flush marrow cells from one murine tibia and femur into a flask containing 9 ml of growth medium. The cultures were maintained in a fully humidified incubator, 5% $CO_2$ atmosphere, at 33° C. Weekly feeding was performed by replacement of the spent medium and non-adherent cells with 10 ml of fresh medium. Where specified, the medium also contained $10^{-5}$ M hydrocortisone sodium hemisuccinate, to facilitate development and maintenance of the adherent cells.

Cultures of the stromal bone marrow cells were established in the same fashion. However, the supplemental horse serum (25%) was replaced with 20% fetal bovine serum as a supplement to Fischer's medium (pH 7.0) and the antibiotic solution as described above. These culture conditions do not allow survival of colony forming units-granulocyte/erythrocyte/macrophage/megakaryocyte (CFU-GEMM) or GM-CFC (confirmed by removing the adherent cells from three cultures and testing for the presence of CFU-GEMM or GM-CFC). In all other respects, the cultures were initiated and maintained as described above.

C. Granulocyte/Macrophage Progenitor Cell (GM-CFC) Assay. This assay was carried out using the method of T. K. Schmalbach et al., Cancer Res., 49, 2574 (1989), but with the following modifications. Bone marrow cells were harvested from untreated mice, and in the LTBMC experiments, the pokeweed nitrogen-stimulated spleen cell-conditioned medium (PWM-SCCM) was replaced with 500 $\mu$l of supernatant harvested from the drug treated (or control) LTBMC. Granulocyte/macrophage colonies (>50 cells) were counted on day 7 with the aid of a dissecting microscope. The morphology of the cells in the colony was verified by removing the colonies from the media with a finely drawn pipet, resuspending the colony in 0.4 ml of media ($\alpha$-MEM or Fischer's) supplemented with 1-5% serum (horse or FBS), spinning the colony onto a slide with a Cytospin centrifuge (500 rpm for 5 min.), and staining with Wright-Giemsa stain. Positive (maximally stimulating amounts of PWM-SCCM included in the culture medium) and negative (no mitogen added) controls were included with each assay. The formation of colonies under these conditions was indicative of colony-stimulating activity in the LTBMC supernatants.

D. Determination of Colony Stimulating Activity (CSA) in Media of Drug-Treated LTBMC. The cultures were allowed to grow for 5 to 6 weeks prior to experimentation. Twelve cultures were randomly divided into four groups (control, DDTC, CBDCA, and CBDCA followed by DDTC), 3 cultures per group. Drug solutions were prepared immediately prior to use with unsupplemented medium and filter sterilized. CBDCA (300 $\mu$M in 10 ml medium) was applied to CBDCA- and CBDCA/DDTC-treated groups while the control and DDTC-treated groups received medium only. Cultures were replaced in the incubator for one hour. The medium/drug solution was then removed and DDTC (300 $\mu$M in 10 ml medium) was added to DDTC and CBDCA/DDTC groups, while the control and CBDCA cultures received medium only. After one hour, these solutions were removed, and 10 ml of supplemented Fischer's medium were added to each culture. At the specified time, this medium, along with any non-adherent cell groups, was removed, and the cells were pelleted by centrifugation (800×g for 5 min.). The supernatants were subsequently evaluated for colony-stimulating activity in the GM-CFC assay as described above.

A similar procedure was used to determine the response of drug-treated cultures exposed to mitogen stimulation. In these experiments, Salmonella typhosa lipopolysaccharide B (5 μg/ml) was added in place of drug to the supplemented Fischer's medium following drug treatment. At the specified times, the medium was removed and tested for colony-stimulating activity as described above.

The CSA production stimulated by various doses of DDTC was determined by treating triplicate cultures with the specified concentration of DDTC or media alone for one hour. This solution was then replaced with supplemented Fischer's medium. Forty-eight hours later, the medium was removed, non-adherent cells were pelleted by centrifugation, and the supernatant was tested for colony-stimulating activity.

E. Results. After 5 weeks, the LTBMC were treated with DDTC with or without prior treatment with CBDCA. At various times, the supernatants were removed and the colony-stimulating activity (CSA) of each supernatant was assessed by using it to replace the pokeweed mitogen-stimulated spleen cell conditioned medium in the GM-CFC assay. Basal levels of granulocyte/macrophage colony-stimulating activity (CSA) in control supernatants varied with each experiment, since differences in serum constituents are known to affect the ability of LTBMC to support hematopoiesis. Enhancement of CSA in three separate experiments is summarized in Table 3.

TABLE 3

ENHANCEMENT OF GM-CSA BY SUPERNATANTS REMOVED FROM MURINE LTBMC

| Removal Time (hr) | CBDCA | DDTC | CBDCA + DDTC | Pokeweed Mitogen (PWM)** |
|---|---|---|---|---|
| 24 | 1.0 ± 0.1 | 3.9 ± 0.7 | 2.6 ± 0.4 | 8.6 ± 1.9 |
| 48 | 1.2 ± 0.2 | 3.4 ± 0.7 | 3.0 ± 0.6 | 6.6 ± 2.2 |
| 72 | 1.1 ± 0.1 | 3.3 ± 0.5 | 2.9 ± 0.5 | 8.2 ± 2.2 |
| 96 | 0.8 ± 0.1 | 4.7 ± 1.7 | 3.9 ± 1.1 | 8.9 ± 3.1 |
| Combined | 1.0 ± 0.1 | 3.8 ± 0.5 | 3.1 ± 0.4 | 8.1 ± 1.2 |

*Results are ratio of colonies/$10^5$ cells using supernatants from treated LTBMC compared to control LTBMC treated with growth medium alone, Mean ±SEM from three experiments at each time point.
**Positive control.

CSA was augmented almost 4-fold in supernatants from DDTC-treated cultures, and this level represented about 50% of the maximal stimulation observed with conditioned medium (PWM-SCCM). CBDCA had no significant effect on CSA either alone or when added just prior to DDTC treatment. DDTC enhanced CSA at concentrations from 100–1000 μM. These concentrations are readily achieved in the plasma of patients treated with DDTC, as demonstrated by R. Qazi et al., *J. Nat. Cancer Inst.*, 80, 1486 (1988).

EXAMPLE III

To determine whether or not DDTC is enhancing production of a factor(s) that stimulates progenitor cells, two different agents known to have CSA were evaluated in combination with DDTC. Addition of hydrocortisone hemisuccinate to the DDTC-treated cultures neither enhanced or diminished DDTC-induced CSA compared to treatment with DDTC alone (data not shown). Supernatants from cultures treated with a maximally stimulating concentration of LPS (5 μg/ml) induced formation of 195 colonies/$10^5$ cells Neither DDTC, CBDCA, nor the combination of CBDCA and DDTC significantly changed the CSA of these supernatants (190–210 colonies/$10^5$ cells). These results demonstrate that DDTC is inducing production of colony-stimulating factor(s) that is not additive with respect to stimulation by either hydrocortisone or LPS.

EXAMPLE IV

The hematopoietic microenvironment is believed to play a pivotal role in the regulation of blood cell production and differentiation. Stromal cells are most likely responsible for elaborating the colony-stimulating factors that regulate the LTBMC system. Thus, LTBMC containing stromal cells (including monocytes/macrophages) were established by the method of L. H. Williams et al., *Exp. Hematol.*, 16, 80 (1988). The cells growing in these cultures were plated in standard clonogenic assays, and no progenitor or stem cell growth was observed, thereby confirming the absence of hematopoietic progenitor cells. Untreated supernatants from these cultures had greater CSA compared to those obtained from the complete LTBMC, and DDTC treatment enhanced CSA approximately twofold compared to untreated cultures. Again, CBDCA treatment had no significant effect on untreated or DDTC treated cultures. These data indicate that DDTC stimulation of CSA is most pronounced during the first 24 hours after treatment. This was confirmed by comparing the CSA of supernatants collected over varying time intervals. CSA was significantly enhanced by DDTC in supernatants collected between 0–8 hours and 8–24 hours after DDTC treatment but was not significantly different from untreated supernatants obtained during later time intervals (data not shown).

The results of Examples II–IV indicate that DDTC modulates hematologic toxicity by inducing stromal cell production of a factor or factors that stimulate hematopoiesis. Although DDTC stimulates proliferation of both stem cells and GM progenitors in vivo only after damage or inhibition of the blood-forming cells of the bone marrow has occurred, e.g., via pretreatment with a myelotoxic drug, CSA was increased by exposure to DDTC alone in vitro. Treatment of LTBMC with a cytotoxic concentration of CBDCA had no effect on CSA, and CBDCA neither enhanced nor inhibited the DDTC response in vitro. These results are consistent with a mechanism in which DDTC augments rather than initiates a proliferative response. The response is presumably initiated by cytotoxic drug in vivo and by the addition of fresh medium in vitro. The involvement of stromal cells in the DDTC response may also account for the variable results observed with different cytotoxic agents, because direct toxicity to stromal cells would be expected to reduce the DDTC response.

EXAMPLE V

Enhanced HLTBMC Production of Hematopoietic Cytokines Following Treatment with DDTC A. Establishment of Human Long Term Bone Marrow Cultures (HLTBMC). Bone marrow cells were aspirated from the posterior iliac crest of normal male volunteer donors and immediately transferred to heparinized blood collection tubes. The cells were diluted 1:1 with McCoy's 5A medium containing 10% FBS. The marrow was further diluted with dextran (4.5% w/v, 3 ml diluted marrow: 1 ml dextran) and allowed to settle for 45 min at which time the buffy coat cells were drawn off. The cells were spun at 1000 rpm for 5 min, supernatant discarded, and then washed 3X with McCoy's 5A medium containing 10% FBS. The marrow was seeded at a density of $1.3 \times 10^7$ nucleated cells per 25 cm$^2$ flask in 8 ml of the long term culture medium (LTCM). The composition of the LTCM was as follows: McCoy's 5A medium with L-glutamine, 12.5% equine serum, 12.5% FBS, sodium bicarbonate (0.075%), sodium pyruvate (1X), vitamin solution (1X), penicillin (100 U/ml)/ streptomycin (100 μg/ml) solution, essential amino acid solution (0.4X], non-essential amino acid solution (0.4X), and $10^{-6}$ M hydrocortisone. The cells were incubated for 9–10 days in a fully humidified 5% $CO_2$ incubator at 37° C. The cells were then fed by aspirating all of the medium from the flask and replacing it with 8 ml of fresh LTCM. The flasks were transferred to another fully humidified 5% $CO_2$ incubator at 33° C. and incubated until confluent (6–7 days).

B. Dithiocarbamate Treatment of HLTBMC. The confluent cultures were divided into two groups (control or DDTC-treated), 3 cultures/group. DDTC solutions were prepared immediately before use and filter sterilized by passage though a 0.22 μm filter. The LTCM was completely aspirated from the cultures and either 8 ml of McCoy's 5A dilute medium (control) or McCoy's containing DDTC (3, 30, 100, or 300 μM) was added and the cultures incubated at 33° C. for 1 hr. The DDTC solution was removed and replaced with 8 ml of LTCM. At the appropriate time point, the conditioned medium was removed and centrifuged at 800×g for 5 min to remove any non-adherent cells. The conditioned medium was transferred into sterile microfuge tubes in 1 ml aliquots and frozen at −20° C. until used in a GM-CFC or ELISA assay.

C. Human GM-CFC Assay. Bone marrow aspirates were harvested from normal volunteers as described previously and diluted 1:1 with McCoy's 5A medium containing 10% FBS. The diluted marrow was layered on top of Ficoll-Paque in a 15 ml centrifuge tube and spun at 1600 rpm for 30 min. The lymphocyte layer was extracted, transferred to a fresh 15 ml centrifuge, and washed 3X with McCoy's medium plus 10% FBS. The cells were resuspended in 10 ml of McCoy's medium +10% FBS, plated in a 25 ml flask, and incubated at 37° C. for 1 hr. The non-adherent cells were transferred to a second 25 ml flask and incubated for another hour at 37° C. This two-step adherence removed a large portion of the monocyte population.

The number of nucleated cells was determined using Turk's solution (typically $5-10 \times 10^6$ nucleated cells/ml). One hundred μl of HLTBMC culture medium (20% v/v) was added to each of the wells in a 4 well multidish Nunclon plate. A GM-CFC mix was prepared by adding the volume necessary to achieve a final concentration of $1 \times 10^5$ nucleated cells/ml to 2X IMDM (25% v./v), FBS (30% v/v), deionized BSA (10% v/v), and agar (1.4% w/v). One-half ml of this mix was added to each of the wells and allowed to harden at room temperature for 20 min. Two ml of sterile double distilled $H_2O$ was placed in the center space of the 4 well plates and the cultures were incubated for 10 days at 37° C. in a fully humidified 5% $CO_2$ incubator. Colonies of >30 cells were counted using a dissecting microscope.

D. Elisa Assays. ELISA assay kits were purchased from various vendors as noted supra. Colony stimulating factor concentrations were determined according to the methods provided with each assay kit. Briefly, a 96 well plate was coated with an antibody specific for the cytokine in question. One hundred μl of the HLTBMC culture medium (CM) was added to the appropriate wells and incubated at 37° C. The wells were washed 4X and an antibody-enzyme conjugate was added. Following a washing step, the wells were incubated with a chromagen, which is oxidized by an enzyme reaction to form a colored complex. The reaction was stopped by the addition of acid and the plate read with a Dynatech ELISA reader. The data were calculated using linear regression analysis in the case of the GM-C_F, and curve fitting programs in the case of G-CSF, IL-1β, TNF-α, and IL-6.

E. Results. The results of the assays performed in section D are summarized on Table 1, supra. Additionally, the formation GM-CFC (granulocyte/macrophage colonies) was enhanced 18-fold by treatment of fresh human bone marrow cells with DDTC-treated HLTBMC supernatants collected at 12, 24, and 48 hr after DDTC exposure (30 μM, 1 hr).

These results represent the first example of bone marrow proliferation resulting from induction of colony-stimulating factor(s) by a small molecule. Thus, the production of a number of factors having G/M cell CSA can be accomplished in vitro by adding to the culture medium of an in vitro, established bone marrow culture a growth factor-stimulating amount of a previously described compound of the formula I ($R^1R^2N(CS)SM$) Preferably about 0.1 to about 1.0 millimole, e.g., about 0.2 to 0.5 millimole, of the compound per liter of culture medium is used. The compound is then separated from the thus-treated culture, fresh culture medium is added to the thus-treated culture, and the concentration of growth factor or factors is permitted to accumulate in the fresh medium. This concentration appears to reach a peak in 8 to 72–96 hours (e.g., 24–48 hours) and then declines, because the growth factor or factors are continuously consumed or utilized by the treated culture. The growth factor or factors can then be isolated by removing the fresh medium from the treated bone marrow culture, and performing conventional steps used to concentrate and purify cytokines.

Accordingly, this invention contemplates in vivo or in vitro stimulation of one or more bone marrow cell growth factors (having G/M cell CSA) via the exposure of bone marrow cells to small amounts of one or more of the previously-described dithiocarbamic compounds of the formula $R^1R^2N(CS)SM$. Hence, this invention can provide a surprisingly simple alternative to the use of cytokines such as the interleukins, and other highly complex cell growth stimulating factors which are difficult to synthesize in quantity without resorting to the use of genetically-engineered organisms. Therefore, the stimulation and proliferation of other cells which has been accomplished using interleukins and the like in the past, can be accomplished using thiocarbamates of formula I. For example, the stimulation and proliferation of LAK cells or of T-helper cell populations can also be accomplished in accord with the present invention.

The administration of DDTC or other dithiocarbamic compounds of the formula $R^1R^2N(CS)SM$ for this purpose is particularly attractive in view of the low toxicity of these compounds, their high solubility in ordinary pharmaceutically acceptable media such as water, and their extraordinary efficacy in stimulating G/M cell CSA at very low doses. Dosage units of this invention are ideal for time-intensive as opposed to time-diffusive use, i.e., essentially single-dose use. That is, the entire dose, undivided or divided into less that 5 or 10 increments, is administered over a very short period of time, e.g., less than 24 hours and preferably less than 8 hours (most preferably by a single injection) and preferably only in response to—and within 24 hours (preferably within 8 hours) of—an insult to the bone marrow (such as a radiation treatment or an anticancer treatment). This time-intensive use is easily distinguishable from continuous dosing and is particularly different from long-term regimens in which a compound is given repeatedly over a period of several days or weeks or in some other time-diffusive manner typically involving small doses.

All of the documents cited hereinabove, including the cross-referenced parent applications, are incorporated by reference herein. The invention has been described with reference to various specific and preferred embodiments and techniques. However, it should be understood that many variations and modifications may be made while remaining within the spirit and scope of the invention.

What is claimed is:

1. A method for protecting and stimulating proliferation of transplanted cells in the bone marrow of a human recipient of a bone marrow transplant, wherein prior to the bone marrow transplant, the recipient has received a myelosuppressing amount of an anti-cancer drug, said process comprising administering to the recipient an amount of a dithiocarbamate compound of the formula:

wherein $R^1$ and $R^2$ are the same or different $(C_1-C_6)$ aliphatic, $(C_5-C_{10})$ cycloaliphatic or one of $R^1$ and $R^2$, but not both, can be H, and M is H or one equivalent of a pharmaceutically acceptable cation, in which case the rest of the molecule is negatively charged, or M is

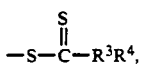

wherein $R^3$ and $R^4$ are defined in the same manner as $R^1$ and $R^2$; wherein said amount effectively counteracts myelosuppression caused by the anti-cancer drug and causes bone marrow cell proliferation by the induction of one or more bone marrow cell growth factors.

2. The method of claim 1 wherein said factors comprise tumor necrosis factor, interleukin-6, interleukin-$1\beta$, granulocyte colony stimulating factor, granulocyte/macrophage colony stimulating factor or mixtures thereof.

3. The method of claim 1 wherein the dithiocarbamate is administered in a dosage unit of about 0.3-30 mg/kg of body weight.

4. The method of claim 1 wherein the dithiocarbamate compound is administered in a dosage unit of less than about 10 mg/kg of body weight.

5. The method of claim 1 wherein the dithiocarbamate compound is administered orally.

6. The method of claim 1 wherein the dithiocarbamate is administered parenterally, in combination with a pharmaceutically acceptable liquid carrier.

7. The method of claim 1 wherein $R^1$ and $R^2$ are both $(C_1-C_6)$alkyl, or $R^1$ is $(C_1-C_6)$alkyl and $R^2$ is a polyhydroxy-substituted $C_6$-alkyl group.

8. The method of claim 1 wherein $R^1$ and $R^2$ are ethyl, and M is an alkali metal cation.

9. The method of claim 1 wherein the dithiocarbamate compound is sodium diethyldithiocarbamate.

10. The method of claim 1 wherein the dithiocarbamate compound is disulfiram.

* * * * *